United States Patent [19]
Hsieh

[11] Patent Number: 5,334,812
[45] Date of Patent: Aug. 2, 1994

[54] SYRINGE NEEDLE DESTRUCTOR

[76] Inventor: Ch'ing-Lung Hsieh, 6F-3, No. 20, Wu-Chyuan-Er Rd, Shin Juang City, Taipei County, Taiwan

[21] Appl. No.: 812,006

[22] Filed: Dec. 23, 1991

[30] Foreign Application Priority Data
Jul. 5, 1991 [CN] China ............................. 91217107.3

[51] Int. Cl.⁵ ............................................. B23K 11/22
[52] U.S. Cl. ........................................................ 219/68
[58] Field of Search ............................ 83/944; 219/68

[56] References Cited
U.S. PATENT DOCUMENTS

| | | | |
|---|---|---|---|
| 4,628,169 | 12/1986 | Ch'ing-Lung | 219/68 |
| 4,877,934 | 10/1989 | Spinello | 219/68 |
| 4,961,541 | 10/1990 | Hashimoto | 219/68 |
| 4,965,426 | 10/1990 | Colombo | 219/68 |
| 5,076,178 | 12/1991 | Kohl et al. | 219/68 |
| 5,091,621 | 2/1992 | Butler | 219/68 |

Primary Examiner—Geoffrey S. Evans
Attorney, Agent, or Firm—Jacobson, Price, Holman & Stern

[57] ABSTRACT

A syringe needle destructor consists of a housing with a multiple-electrode type needle destroying device in the housing and an elastic needle supporting frame disposed above the housing over the destroying device. The frame consists of a sliding face plate with a needle inserting hole and an elastic frame body. The housing is provided with an opening to contain a number of electrode members of the destroying device. Two snap holes are provided on two sides of the opening to install the elastic supporting frame. The opposite inner edges of the snap holes are provided with spring grooves to support two springs of the supporting frame respectively. The needle destroying device has at least two electrode members in the housing connected to the power source. Different electrode configurations are disclosed.

9 Claims, 5 Drawing Sheets

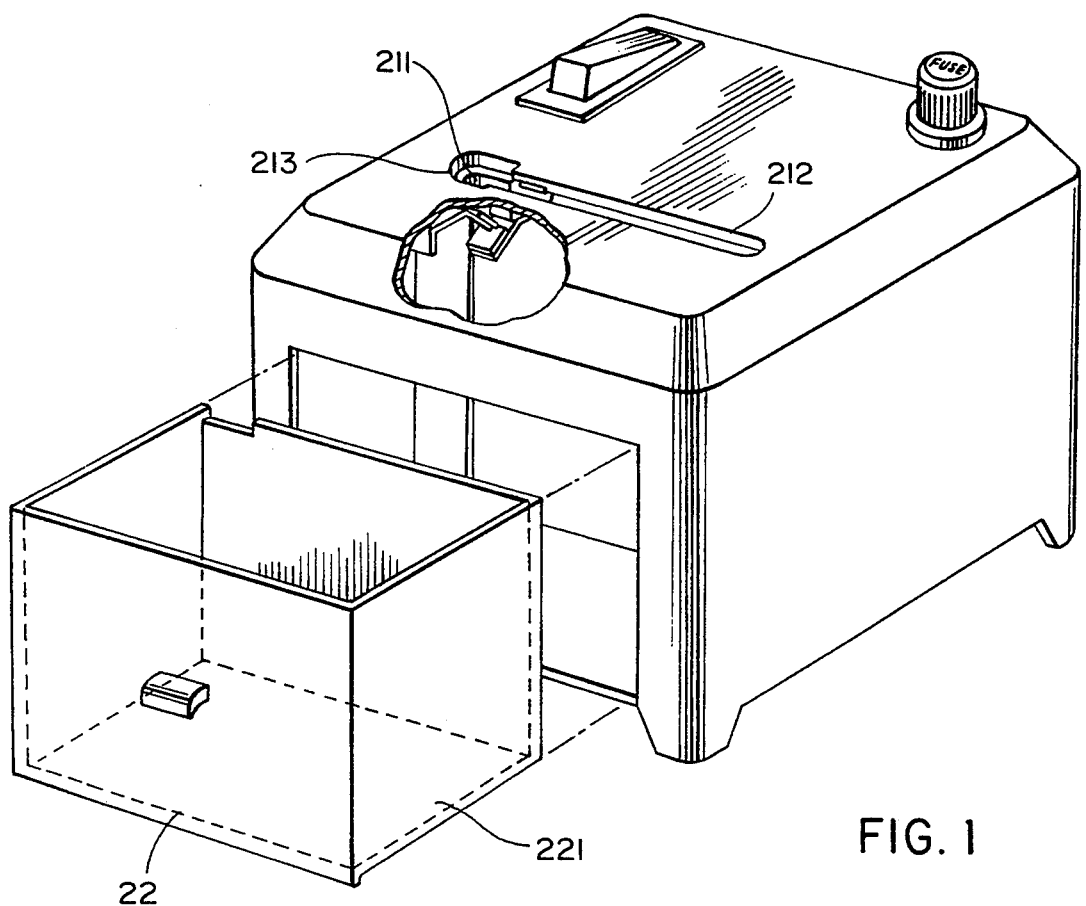
FIG. 1
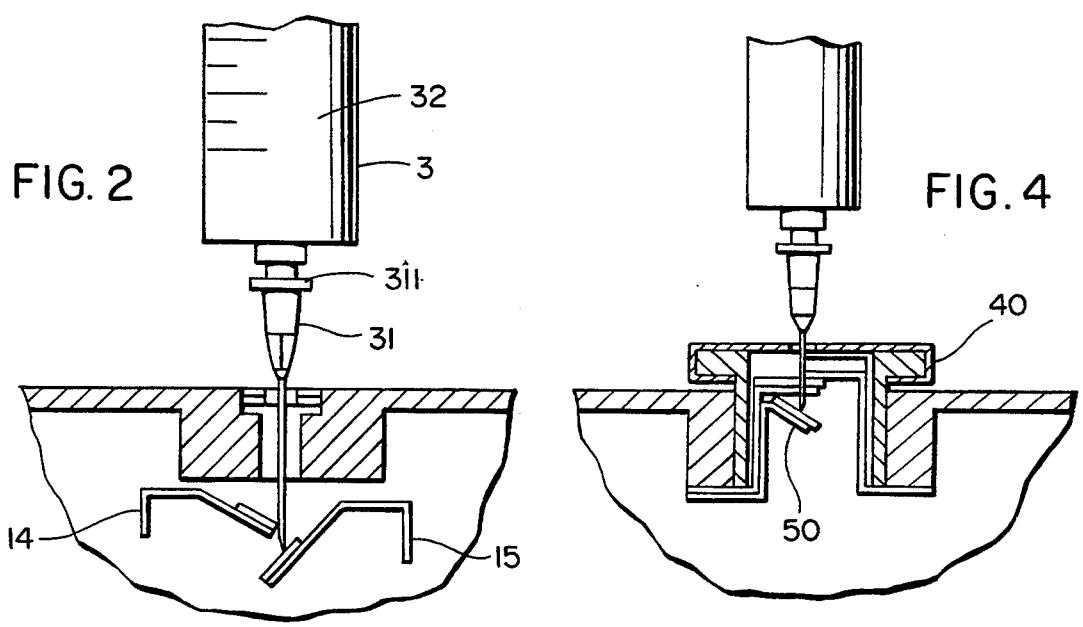
FIG. 2
FIG. 4

SYRINGE NEEDLE DESTRUCTOR

BACKGROUND OF THE INVENTION

The present invention is a syringe needle destructor which can quickly destroy the syringe needle and prevent the residual injection fluid in the needle cap from flowing out.

The syringe needle is the daily necessity in the department of medical health which uses it in quantities. Since the needle tip is too sharp and some residual injection fluid will leave in the needle cap, if directly discarded the used syringe in the trash, it is not only easy to hurt the people but also very unhealthful to them; therefore, as a rule, before discarding, it has to be disposed of. A pocket syringe needle destructor (Application No. 7,228,127 patented in Taiwan) has been patented in a number of countries in Europe and America where its marketing is booming. The said syringe needle destructor, as shorn in FIGS. 1 and 2, consists of a housing 21, a needle collector 22 in the housing 21, and two electrodes 14, 15 which are indented but not contacted. A needle supporting frame device above the housing 21 consists of a needle inserting hole 211 and a horse-shoe shaped supporting frame 213 of which the width is the same as that of a needle sliding track 212. The needle inserting hole 211 is a round hole above the two electrodes 14, 15, and the horse-shoe shaped supporting frame 213 is disposed inside the needle inserting hole 211 and at the needle sliding track 212 but slightly lower than them, with the same width as that of the needle sliding track 212, slightly smaller than the needle shoulder 311 but slightly larger than the other part of needle. The operating principle thereof is so: when to destroy the needle 31, first to insert the needle 31 in the needle inserting hole 211 so as to contact the two electrodes 14, 15 to form a loop wherefrom the high temperature generated from the current melts down and distorts the needle 31 instantaneously so that the syringe 3 moves down and the needle shoulder 311 contacts and stops at the supporting frame 213, then the barrel 32 with needle 31 slides toward one side of the needle sliding track 212, and during sliding, the needle 31 destroyed, distorted and caught below the needle sliding track 212 disengages from the barrel 32 and falls down to the metal plate 221 of needle collector 22 in the housing, then the operating processes of destroying, disengaging and collecting the needle 31 are convenient and quick but the following problems remain existing:

1. When proceeding with the destruction of needle 31, strong sparks and firelight emit out from the needle inserting hole 211 and the needle sliding track 212 and lead to a extremely psychological unrest of the user frequently.

2. If the head ring of needle cap is extremely small or there is no needle cap at all, it is inconvenient to use such an equipment.

3. The waste needle head in the needle collector has the needle cap wherein some residual injection fluid or blood more or less exists. If not quickly eliminate the needle head, a bad odor will be generated in the needle destructor a while later to affect the human health unfavorably.

4. After the destroyed needle with plastic needle cap falls down into the needle collector 22, the blazing red-hot metal chips of needle cap of following needle under destruction will always fall down to the previously destroyed plastic needle caps in the needle collector 22, leading to burning these plastic needle caps and belching poisonous smoke to pollute the environment.

5. If the barrel and needle of syringe are integrally molded or thread-engaged with each other, the needle cannot disengage from the barrel after destruction, and the melted-down needles will form a mass of red-hot metal chips between the two electrodes 14, 15 and have to be taken out together with their barrels from the syringe needle destructor, and when discarding them, they tend to burn the people or ignite the trash, so it is very inconvenient to discard same.

SUMMARY OF THE INVENTION

The object of the present invention is to offer a syringe needle destructor with a new structure which is suitable for various needles with different shapes and specifications which is characterized by quick destruction, much less firelight and sparks emitting out, neither burning the people nor igniting the trash when discarding same, and with substantial no pollution of residual injection fluid and poisonous fumes.

The present invention consists of a housing, a multi-electrode type needle destroying device and a needle supporting frame, which is characterized by the following: the needle supporting frame is an elastic supporting frame disposed above the housing and right above the destroying device and consists of a sliding plate and an elastic frame, an opening on the housing can exactly contain the plural electrode members of the multi-electrode type needle destroying device, one snap hole each on the two sides of the opening is designed to mount the elastic supporting frame, each of opposite inner edges of these snap holes is provided with a spring groove to support the spring of the elastic supporting frame, and the multi-electrode type needle destroying device consists of at least two electrode members in the housing which are connected to same one power source and able to form two loops, and such electronic components as power source wire, switch, transformer and fuse.

The foregoing two electrode members at least may be three-piece electrodes in the shape of flat plate or two-piece multi-layer electrodes or in various geometrics but they have to be derided into two sets so as to form two circuit loops in keeping with the said electronic components and needle.

The operating principle of the present invention is as follows: the destroyed needle is inserted in through the inserting hole of elastic supporting frame. Since the elastic supporting frame has a fine elastic tension, it may be pressed down when subject to a foreign force and can restore its original position when the foreign force disappears, so it can lower the probability of emitting the firelight and sparks generated when starting the destruction of needle from the inserting hole and can destroy the needle up to the shortest extent (about 2 mm from the needle cap); the two sets of electrodes consist of two or three electrode members and the destroyed needle can form two loops: the inserted needle and one set of electrodes form a loop first which generates high temperature quickly to destroy the needle when the large current passes through it instantaneously, so the needle under the action of elastic supporting frame moves down to be continuously destroyed until the elastic supporting frame presses down to utmost, namely, somewhere about 2 mm from the needle cap, and then lifts up the syringe; meantime, the high-temperature, distorted waste needle destroyed into the metal chips is connected to another set of electrodes to form a second loop and quickly generate high temperature to melt down the waste needle which falls down into the needle collector in the housing, the shortest residual needle head below the needle cap is sealed at its tubular opening under the high temperature melting, so some injection fluid and the patient blood residually left in the needle cap will never flow out, and the problem of environment pollution may be solved. So far as the syringe with needle is concerned, the needle attached, to the needle cap after destruction is only 2 mm, so the said syringe taken out from the housing can quickly lower its temperature and radiate its heat and not ignite the trash bin or burn people.

The present invention can be designed to have a needle inserting hole with changeable diameter and shape so that the present invention may be suitable for various needles with different shapes and specifications.

BRIEF DESCRIPTION OF THE DRAWINGS

FIG. 1 is an elevational view of the pocket syringe needle destructor.

FIG. 2 is a schematic view of structural principle of the pocket syringe needle destructor.

FIG. 4 is a schematic view of structural principle of Example 1 of the present invention.

DETAILED DESCRIPTION

Figure 3:
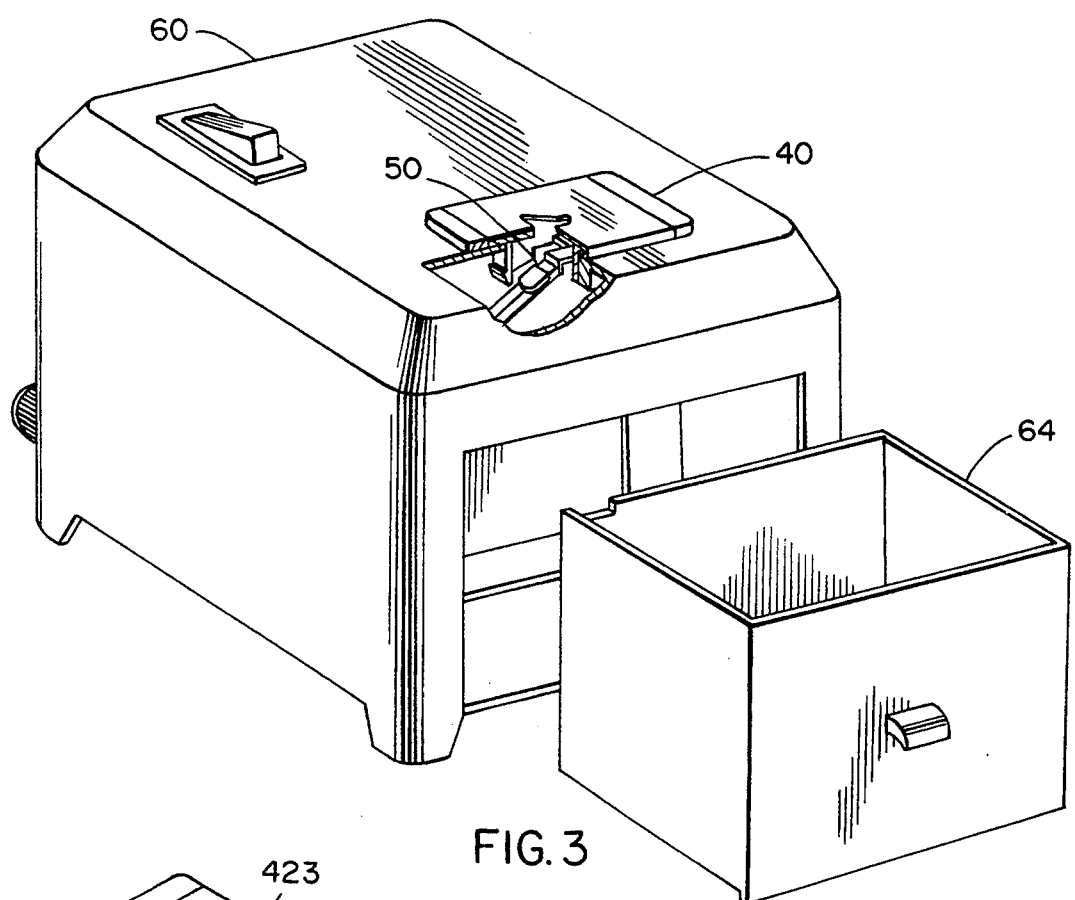
FIG. 3 is an elevational view of Example 1 of the present invention.
Figure 6:
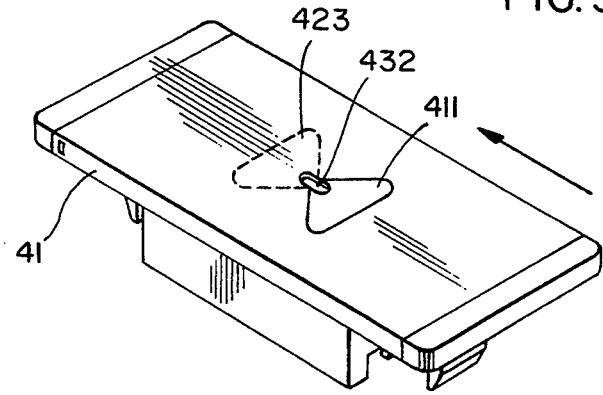
FIG. 6 is as schematic view of the inserting hole in an open state on the supporting frame of Example 1 of the present invention.
Figure 7:
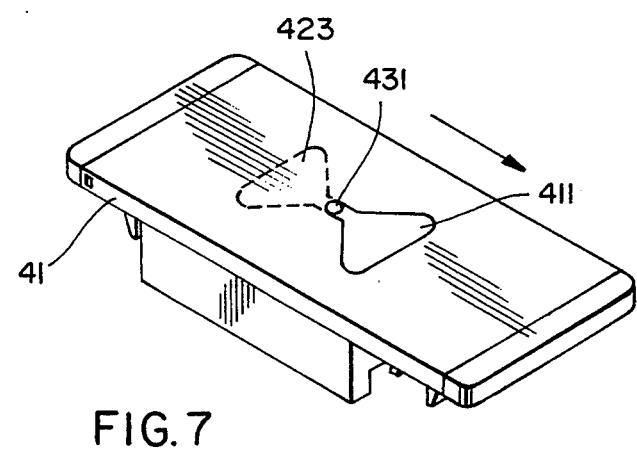
FIG. 7 is a schematic view of the inserting hole in a close state on the elastic supporting frame of Example 1 of the present invention.

As shown in FIG. 3-7, Example 1 of the present invention consists of an elastic supporting frame 40, a multi-electrode type needle destroying device 50 and a housing 60. The elastic supporting frame 40 is installed above the housing 60, the destroying device 50 is installed in the housing 60 beneath the elastic supporting frame 40, and the elastic supporting frame 40 consists of a sliding face plate 41 and an elastic frame body 42 coupled with each other. The sliding face plate 41 is provided with an opening 411 in the shape of a reverse triangle. The front and rear side edges of sliding face plate 41 are respectively folded down to form two corresponding sliding grooves 412, 413, two corresponding notches 412a, 413a are provided to the positions nearby the ends of said two sliding grooves 412, 413. The two ends of a damper 414 pass through and catch between the two notches 412a, 413a. The side edge of sliding face plate 41 on the side corresponding to the damper 414 is suitably folded down to form a stop block 415.

The corresponding inserting rods 416a, 416b, 416a′, 416b′ of two decorative strips 416, 416′ can just catch the two ends 412b, 413b, 412c, 413c of two corresponding sliding grooves 412, 413 on the outer side of damper 414 (or stop block 415). The elastic frame body 42 consists of a frame face 421 with a reverse triangular opening 423 at the center and four-piece linked (or separable) support wall 424 extended down from the four sides below the frame face 421, one corresponding catch 425, 426 is provided to the left and right outer sides of support wall 424, a reciprocating spring 43 is provided between the outer side of catch 426 and the stop block 415 of sliding face plate 41. A face plate 422 is provided to the frame face 421 and provided with a reverse triangular opening 423 which partially and correspondingly overlaps the reverse triangular opening 411 on the sliding face plate 41. When the sliding face plate 41 and the face plate 422 of elastic frame body 42 displace toward the damper 414 and stop block 415, the correspondingly overlapped part of the opening 411 on the sliding face plate 41 and the opening 423 on the face plate 422 of elastic frame body 42 will be able to elastically and retractably form an inserting hole 431 of the size as that of the needle hole or expand up to an inserting hole 432 with a diameter of about 0.5 cm, so the needles of various shapes or different diameters can be inserted in through these two holes 431, 432 to satisfy and meet the demand of various needles. Most inner edge of the opening 411 on the sliding face plate 41 having not overlapped the opening 423 on the face plate 422 of elastic frame body 42 contacts the surface of face plate 422 of elastic frame body 42 to form a guiding ring capable of quickly guiding the needle to insert in the inserting hole 431.

As shown in FIGS. 3-8, the multi-electrode type needle destroying device 50 consists of a power source wire 51, a switch 52, a transformer 43, three electrode members 54, 55, 56 and a fuse 57 which are connected to the home power source 110 V or 220 V. The electrode members 54, 55, 56 consist of outer layers 541, 551, 561 of platinum with high melting point and inner layers 542, 552, 562 of copper respectively. The electrode members 54, 55 are connected to the same one electrode of power source, but the electrode member 56 is connected to another electrode of power source, and an interval of about 0.5-0.7 cm is kept between the electrode members 54, 56. The lowest electrode member 54 and the highest electrode member 56 are correspondingly disposed. The corresponding side of electrode member 54 is inclined down to a suitable angle (about 30°-60°). So the two electrode members 54, 56, transformer 53, switch 52, power source wire 51 and the needle to be destroyed from a loop in order to melt down the needle of syringe. The electrode member 55 is disposed considerably nearby but not to contact the highest electrode member 56. So the electrode member 56, transformer 53, switch 52, power source wire 51 and the needle to be destroyed from another loop in order to melt down the destroyed metal chips of needles in a mass nearby the lower edge of needle cap.

Figure 5:
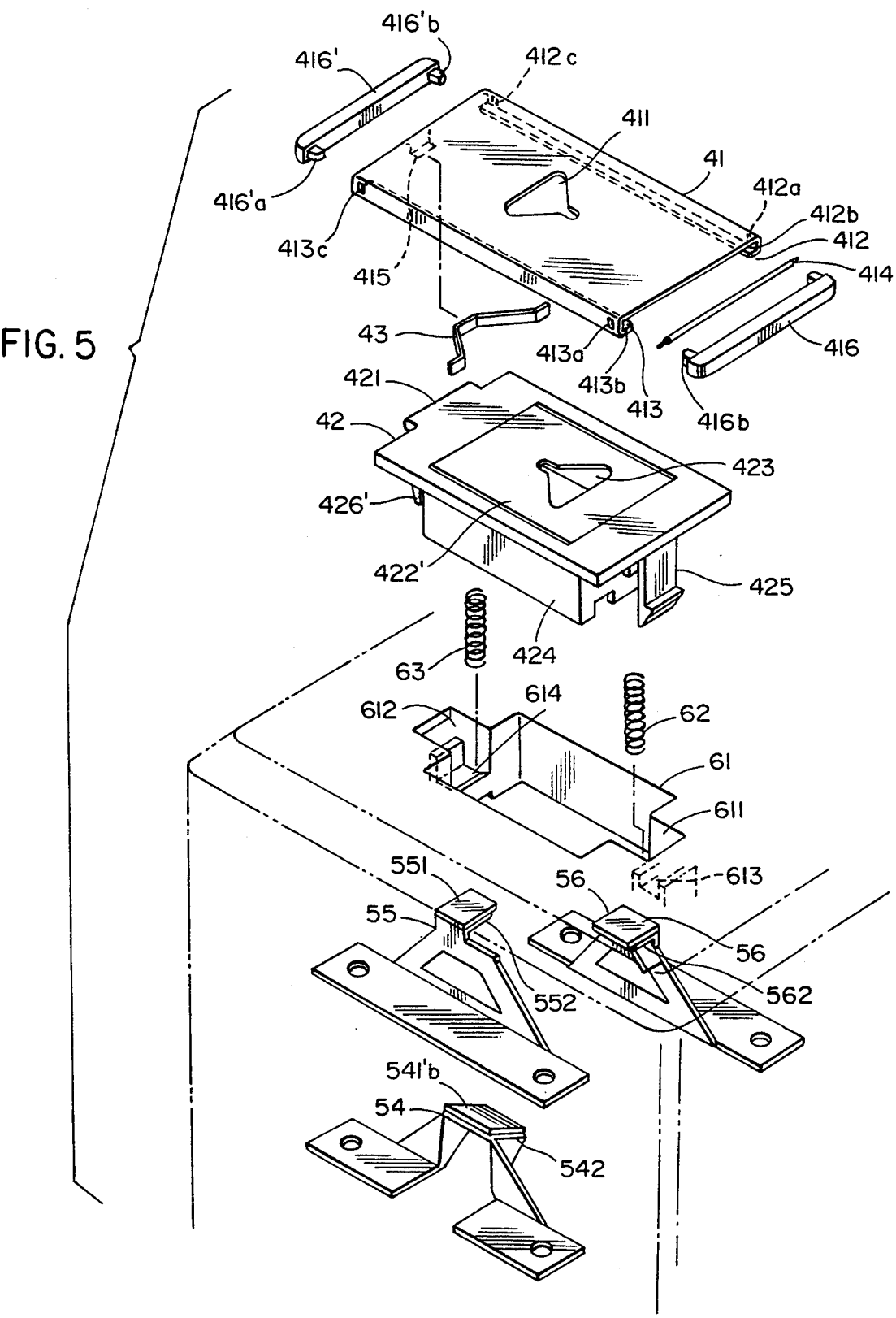
FIG. 5 is a breakdown view of the elastic supporting frame, multi-electrode type needle destroying device and electrode members of Example 1 of the present invention.
Figure 8:
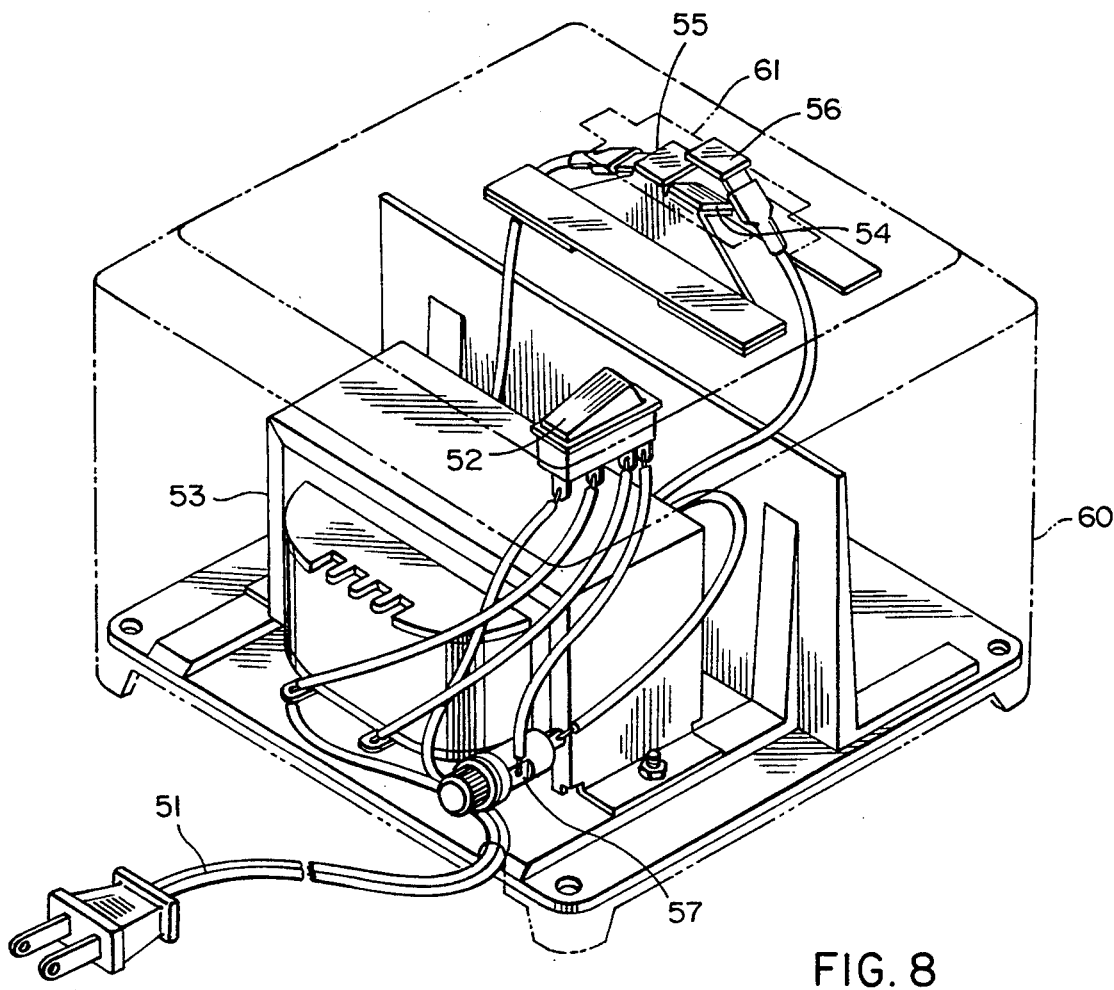
FIG. 8 is a perspective view of the housing and multi-electrode type needle destroying device of Example 1 of the present invention.
Figure 10:
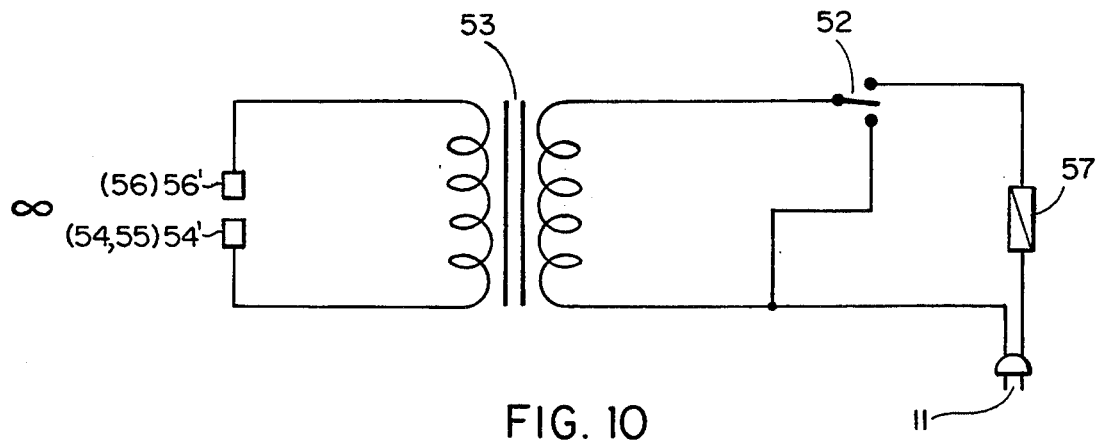
FIG. 10 is an electric wiring diagram of the present invention.

As shown in FIG. 5, the three electrode members 54, 55, 56 of multi-electrode type needle destroying device 50 can just be screwed in a cross opening 61 on the housing 60. A snap hole 611, 612 is provided respectively to the two sides of the cross opening 61, and a spring groove 613, 614 is provided respectively to the opposite inner edges of snap hole 611, 612 to contain a spring 62, 63 which can elastically support the elastic supporting frame 40. When the elastic supporting frame 40 subject to the pressure of foreign force displaces down to fully commpress the spring 62, 63 on the lower edge of two sides of elastic frame body 42, the opening 423 on the face plate 422 of elastic frame body 42 is extremely close to the highest electrode member 56 in the housing 60, so that the needle can be fully melted down (about 2 mm close to the lower edge of needle cap).

When to use this example to destroy the syringe needle, first of all, to slide the needle along the guiding ring and toward the inserting hole 431 and instantaneously insert the needle in the inserting hole 431 so as to contact the lowest electrode member 54. Since the side of electrode member 54 corresponding to the electrode member 56 is inclined down to a angle, the needle slides toward the electrode member 56 and a circuit loop is formed by the needle and two electrode members 54, 56. When the large current passes through this loop, a high temperature is quickly generated to melt down the needle. Under the action of elastic supporting frame 40, the needle moves down on the one hand and is melted down on the other hand until the elastic supporting frame 40 is pressed down to the lowest position, the needle is melted down about 2 mm close to the needle cap. Then the user lifts up the syringe to let the distorted waste needle melted down to metal chips with high temperature contact the electrode members 55, 56, so such a needle, two electrode members 55, 56, and such electronic components as the power source wire 51, switch 52, and transformer 53, form the second current loop to quickly generate a high temperature to melt down the needle. The distorted needle falls down into the needle collector 64. Since the tubular opening of the shortest residual needle is sealed by the high temperature, the residual injection fluid and patient's blood in the needle cap will not flow out any more to pollute our environment. Finally, the residual needle adhered to the needle cap will be only 2 mm long and taken out from the inserting hole 431 (or 432). Since the volume of said residual needle is rather small and the temperature thereof will be quickly radiant and lowered, it will not ignite the trash bin or burn the people. Because the inserting hole 431 is the overlapped part of both openings 423, 411 and the face plate 41 is corresponding to the frame face 421 for sliding, the needles of various diameters and shapes can be inserted in through the inserting hole 431, and then under the action of reciprocating spring 43, the clearance between the inserting hole 431 and the needle is extremely small, the emitting-out sparks or firelight can be considerably decreased.

Figure 9:
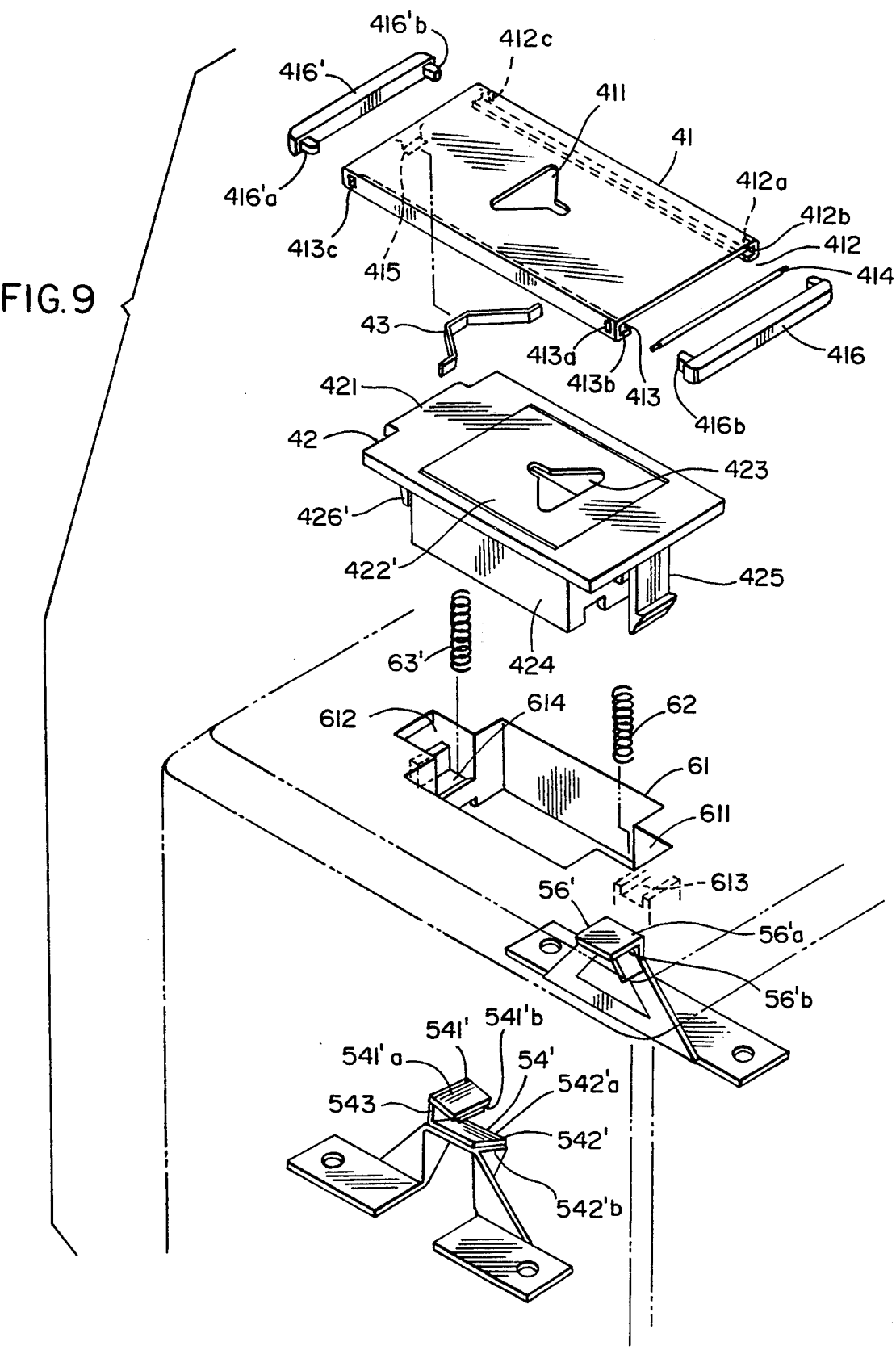
FIG. 9 is a breakdown of the elastic supporting frame, multi-electrode type needle destroying device and electrode members of Example 2 of the present invention.

FIG. 9 shows Example 2 of the present invention which is the same as the above said Example 1 except the structure of electrode members of the multi-electrode needle destroying device. Example 2 has two electrode members: the upper electrode member 56' remains a flat plate type electrode member but the lower electrode member is a two-layer electrode member 54' which consists of an upper-layer electrode member 541', a lower-layer electrode member 542' and a base 543'; both the upper-layer electrode member and the lower-layer electrode member are on the same one side of the base to extend not in parallel, so a suitable contained angle is formed therebetween (about 30°–60°); the upper-layer electrode member 541' is narrower than the lower-layer electrode member 542', the upper-layer and lower-layer electrode members 541', 542' and the electrode member 56' consist of an outer metal layer 541'a, 542'a, 56'a and an inner copper layer 541'b, 542'b, 56'b respectively. The electrode member 56' is connected to one electrode of power source but the two-layer electrode member 54' is connected to another electrode of power source. After the two-layer electrode member 54' and the upper electrode member 56' are thread-engaged in the housing 50, the upper-layer electrode member 541' is parallel with the upper electrode member 56' and extremely close to the latter but not to contact the latter, and the corresponding sides of both the lower-layer electrode member 542' and the upper electrode member 56' incline down to a suitable angle (30°–60°). The function and usage of the two-layer electrode member 54' are the same as those of the electrode members 54, 55 in Example 1.

I claim:

1. A syringe needle destructor which consists of a housing, a multi-electrode type needle destroying device and a needle supporting frame, characterized in that wherein the needle supporting frame is an elastic supporting frame disposed above the housing and installed above the destroying device and consists of a sliding face plate with a needle inserting hole and an elastic frame body the housing is provided with an opening to contain at least two electrode members of the multi-electrode type needle destroying device, two snap holes are provided on the two sides of the opening to install the elastic supporting frame, the opposite inner edges of said two snap holes are provided with two spring grooves to support two springs of the elastic supporting frame respectively, and the multi-electrode type needle destroying device consists of at least two electrode members in the housing, connected to a power source, a power source wire, a switch, a transformer and a fuse.

2. A syringe needle destructor as claimed in claim 1, characterized in that the needle destroying device consists of three electrode members which are each in the shape of a flat plate, connected to said power source and disposed in a certain distance from each other in the housing, a first and a second of said electrodes being vertically displaced and mutually obliquely disposed and a third of said electrodes being horizontally displaced from said first and second of said electrodes.

3. A syringe needle destructor as claimed in claim 1, characterized in that the needle destroying device consists of two electrode members 54', 56' connected to said power source, wherein one electrode member 54 is a multi-layer electrode member, with a lower-layer electrode and an upper layer electrode, the lower layer electrode being disposed a certain distance from the other electrode member and mutually oblique up and down, and the upper-layer electrode 541' of the multi-layer electrode member 54' and the other electrode member 56' are parallel and close to each other.

4. A syringe needle destructor as claimed in claim 1, characterized in that the multi-electrode type needle destroying device consists of three electrode members connected in the housing and connected to same one power source, a first and a second of said electrodes being vertically displaced and mutually obliquely disposed and a third of said electrodes being horizontally displaced from said first and second of said electrodes.

5. A syringe needle destructor as claimed in claim 1, characterized in that an opening is provided to the sliding face plate of the elastic supporting frame, the front and rear sides of sliding face plate are respectively folded down to form two corresponding sliding grooves, two corresponding notches are respectively provided to the ends of two sliding grooves; the two ends of a damper respectively pass through these two notches and catch between these two notches, the side edge of sliding face plate on the side corresponding to the damper is suitably folded to form a stop block; the corresponding inserting rods of two decorative strips catch the two end openings of two sliding grooves on the outer side of the damper; and an opening is provided to the face plate on the frame face of elastic frame body of the elastic supporting frame, and the four sides below the frame face respectively extend down to form four pieces of linked or separable support wall of which the outer left and right sides are respectively provided with a corresponding catch.

6. A syringe needle destructor as claimed in claim 1, characterized in that an opening is provided to the sliding face plate of the elastic supporting frame, the front and rear sides of sliding face plate are respectively folded down to form two corresponding sliding grooves, two corresponding notches are respectively provided to the ends of two sliding grooves; the two ends of a damper respectively pass through these two notches and catch between these two notches, the side edge of sliding face plate on the side corresponding to the damper is suitably folded to form a stop block; the corresponding inserting rods of two decorative strips catch the two end openings of two sliding grooves on the outer side of the damper; and an opening is provided to the face plate on the frame face of the elastic frame body of the elastic supporting frame, and the four sides below the frame face respectively extend down to form four pieces of linked or separable support wall of which the outer left and right sides are respectively provided with a corresponding catch; and the multi-electrode type needle destroying device consists of three electrode members which are each in the shape of a flat plate, connected to said power source and disposed in a certain distance from each other in the housing, a first and a second of said electrodes being vertically displaced and mutually obliquely disposed and a third of said electrodes being horizontally displaced from said first and second of said electrodes.

7. A syringe needle destructor as claimed in claim 1, characterized in that an opening is provided to the sliding face plate of elastic supporting frame, the front and rear sides of sliding face plate are respectively folded down to form two corresponding sliding grooves, two corresponding notches are respectively provided to the ends of two sliding grooves; the two ends of a damper respectively pass through these two notches and catch between these two notches, the side edge of sliding face plate on the side corresponding to the damper is suitably folded to form a stop block; the corresponding inserting rods of two decorative strips catch the two end openings of two sliding grooves on the outer side of damper; and an opening is provided to the face plate on the frame face of elastic frame body of the elastic supporting frame, and the four sides below the frame face respectively extend down to form four pieces of linked or separable support wall of which the outer left and right sides are respectively provided with a corresponding catch; the multi-electrode type needle destroying device consists of two electrode members connected to said power source, the electrode member is a multi-layer electrode member, the lower-layer electrode of multi-layer electrode member and another electrode member are correspondingly disposed to keep a certain distance from each other and be mutually oblique up and down, and the upper-layer electrode member of multilayer electrode member and the electrode member are parallel and close to each other.

8. A syringe needle destructor as claimed in claim 1, characterized in that wherein an opening is provided to the sliding face plate of elastic supporting frame, the front and rear sides of sliding face plate are respectively folded down to form two corresponding sliding grooves, two corresponding notches are respectively provided to the ends of two sliding grooves; the two ends of a damper respectively pass through these two notches and catch between these two notches, the side edge of sliding face plate on the side corresponding to the damper is suitably folded to form a stop block; the corresponding inserting rods of two decorative strips catch the two end openings, of two sliding grooves on the outer side of damper; and an opening is provided to the face plate on the frame face of elastic frame body of the elastic supporting frame, and the four sides below the frame face respectively extend down to form four pieces of linked or separable support wall of which the outer left and right sides are respectively provided with a corresponding catch; and the multi-electrode type needle destroying device consists of three electrode type needle destroying device consists of three electrode members connected in the housing and connected to said power source, a first and a second of said electrodes being vertically displaced and mutually obliquely disposed and a third of said electrodes being horizontally displaced from said first and second of said electrodes.

9. A syringe needle destructor as claimed in claim 1, characterized in that the sliding face plate of elastic supporting frame is coupled onto the elastic frame body, the four sides below the frame face of elastic frame body respectively extend down to form four pieces of linked or separable support wall of which the outer left and right sides are respectively provided with a corresponding catch, a reciprocating spring is disposed between the outer side of one catch and the stop block of sliding face plate; the opening on the sliding face plate of elastic supporting frame and the opening on the face plate of elastic frame body are partially and correspondingly overlapped to form a hole of which the size and shape may become an inserting hole; and that part of opening on the sliding face plate having not overlapped the opening on the face plate of elastic frame body forms a guiding ring of needle inserting hole on the surface of face plate of elastic frame body.

* * * * *